(12) United States Patent
Okamoto et al.

(10) Patent No.: US 10,315,022 B2
(45) Date of Patent: Jun. 11, 2019

(54) CO-INJECTION MEMBER (71) Applicant: Nikkiso Company Limited, Tokyo (JP)

(72) Inventors: Shingo Okamoto, Shizuoka (JP); Kazuhide Ono, Shizuoka (JP); Katsumi Imigi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 307 days.

(21) Appl. No.: 15/178,800

(22) Filed: Jun. 10, 2016

(65) Prior Publication Data
US 2016/0346528 A1 Dec. 1, 2016

Related U.S. Application Data (63) Continuation of application No. PCT/JP2014/082891, filed on Dec. 11, 2014.

(30) Foreign Application Priority Data

Dec. 11, 2013 (JP) .................................. 2013-255518

(51) Int. Cl.
*A61M 39/00* (2006.01)
*A61M 39/04* (2006.01)

(52) U.S. Cl.
CPC .......... *A61M 39/045* (2013.01); *A61M 39/04* (2013.01); *A61M 2206/20* (2013.01)

(58) Field of Classification Search
CPC ................ A61M 39/04; A61M 39/045; A61M 2206/14; A61M 2206/20
See application file for complete search history.

(56) References Cited

U.S. PATENT DOCUMENTS 5,221,271 A * 6/1993 Nicholson ............. A61M 39/04
604/539
5,306,265 A * 4/1994 Ragazzi ................ A61M 39/02
128/912
(Continued)

FOREIGN PATENT DOCUMENTS

JP 2006-129884 A 5/2006
JP 2006-223587 A 8/2006
(Continued)

OTHER PUBLICATIONS

Extended European Search Report, Application No. 14869855.8 dated Sep. 11, 2017.
(Continued)

*Primary Examiner* — Benjamin J Klein
(74) *Attorney, Agent, or Firm* — The Dobrusin Law Firm, PC (57) ABSTRACT

An object is to provide a co-injection member which can smoothly collect a liquid of an internal flow route, which can smoothly inject a liquid into the internal flow route, and which can reliably prevent congestion of the liquid in the internal flow route. A co-injection member includes a main body that can be connected to a blood circuit through which blood is circulated, an internal flow route that is formed inside the main body, and that can circulate the liquid of the blood circuit, an inlet flow route that is formed inside the main body, and that introduces the blood into the internal flow route, an outlet flow route that is formed inside the main body, and that can discharge the blood of the internal flow route, and a rubber member that is attached to an opening formed in the main body, and that separates the inside and the outside of the internal flow route from each other. The co-injection member can collect the blood of the internal flow route and can inject the other liquid into the internal flow route via the rubber member. The inlet flow route
(Continued)

extends while a diameter thereof gradually decreases toward a position shifted from a center of the internal flow route.

17 Claims, 9 Drawing Sheets

(56) References Cited

U.S. PATENT DOCUMENTS

| | | | | |
|---|---|---|---|---|
| 6,468,251 | B1 * | 10/2002 | Yamanaka | A61M 39/02 604/256 |
| 8,715,217 | B2 * | 5/2014 | Frugier | A61M 1/34 604/539 |
| 2008/0199558 | A1 | 8/2008 | Abe et al. | |
| 2013/0237923 | A1 * | 9/2013 | Ueda | A61M 39/045 604/246 |
| 2015/0112271 | A1 * | 4/2015 | Chelak | A61M 39/06 604/186 |

FOREIGN PATENT DOCUMENTS

| | | |
|---|---|---|
| JP | 2009-039158 A | 2/2009 |
| WO | 95/15194 A1 | 6/1995 |
| WO | 96/40359 A1 | 12/1996 |
| WO | 2008/043069 A2 | 4/2008 |
| WO | 2015/087982 A1 | 6/2015 |

OTHER PUBLICATIONS

International Search Report for Application No. PCT-JP2014-082891 (WO2015/087982), dated Feb. 23, 2015.

* cited by examiner

CO-INJECTION MEMBER

FIELD

The present teachings relates to a co-injection member which can collect a liquid from internal flow route or can inject the other liquid into the internal flow route via a rubber member.

BACKGROUND

A blood circuit, which is used for dialysis treatment so as to extracorporeally circulate blood of a patient, is generally configured to mainly include a flexible tube for connecting respective configuration elements to each other, such as a dialyzer and a drip chamber. A co-injection member (also called a "rubber button" or an "access port") is connected to a predetermined position of the blood circuit. The co-injection member is normally configured to have a main body that can be connected to the blood circuit, an internal flow route through which a liquid of the blood circuit can be circulated, an inlet flow route that introduces the liquid into the internal flow route, an outlet flow route that discharges the liquid of the internal flow route, and a rubber member that is attached to an opening formed in the main body.

Then, the blood flowing in the blood circuit can be collected, or a drug or a physiological saline solution can be injected into the blood circuit by a puncture needle of an injection syringe puncturing the rubber member of the co-injection member. Some rubber members of the co-injection member have a slit formed for communication between the inside and the outside of the internal flow route. The blood flowing in the blood circuit can be collected, or the drug or the physiological saline solution can be injected into the blood circuit by inserting a distal end of a puncture tube or a syringe into the slit. However, there is a possibility that flow of the blood may congest the internal flow route. Accordingly, in order to prevent the congestion, in the related art, a co-injection member (refer to PTL 1) has been proposed in which a projection is formed on a bottom surface in a central portion of the internal flow route, or a co-injection member (refer to PTL 2) has been proposed in which the inlet flow route and the outlet flow route are formed toward a position shifted from the center of the internal flow route.

CITATION LIST

Patent Literature

PTL 1: Japanese Unexamined Patent Application Publication No. 2006-129884

PTL 2: Japanese Unexamined Patent Application Publication No. 2009-39158

SUMMARY

However, according to a technique in the related art disclosed in PTL 1, in a case where the distal end of the puncture tube or the syringe is inserted into the slit of the co-injection member, the distal end interferes with the projection, thereby causing a possibility that the blood cannot be satisfactorily collected, or the drug, cannot be satisfactorily injected The blood flowing in the internal flow route collides with the projection, thereby causing a possibility that a blood cell component in the blood may be adversely affected. In addition, according to a technique in the related art disclosed in PTL 2, although the congestion can be inhibited to some degree by forming a vortex inside the internal flow route, flow velocity of the blood flowing in the internal flow route is not changed. Consequently, there is a problem in that an effect for inhibiting the congestion of the blood in the internal flow route is insufficiently obtained.

The present teachings are made in view of these circumstances, and aims to provide a co-injection member which can smoothly collect a liquid of an internal flow route, or which can smoothly inject the liquid into the internal flow route, and which can reliably prevent congestion of the liquid in the internal flow route.

According to the teachings herein includes a co-injection member includes a main body that can be connected to a circulation line through which a liquid is circulated, an internal flow route that is formed inside the main body, and that can circulate the liquid of the circulation line, an inlet flow route that is formed inside the main body, and that can introduce the liquid into the internal flow route, an outlet flow route that is formed inside the main body, and that can discharge the liquid of the internal flow route, and a rubber member that is attached to an opening formed in the main body, and that separates the inside and the outside of the internal flow route from each other. The co-injection member can collect the liquid of the internal flow route and can inject the other liquid into the internal flow route via the rubber member. The inlet flow route extends while a diameter thereof gradually decreases toward a position shifted from the center of the internal flow route.

According to the teachings herein, in the co-injection member described in the teachings herein, the rubber member may include a slit through which the inside and the outside of the internal flow route communicate with each other.

According to the invention described in the teachings herein, in the co-injection member described in the teachings herein, the outlet flow route may extend while a diameter thereof gradually decreases toward the position shifted from the center of the internal flow route.

According to the teachings herein, in the co-injection member described in the teachings herein, the inlet flow route and the outlet flow route may have a symmetrical shape with respect to the center of the internal flow route, while respective connection portions connected to the circulation line are coaxially formed.

According to the teachings herein, in the co-injection member described in the teachings herein, the circulation line may include a blood circuit, which extracorporeally circulates and purifies blood of a patient.

According to the teachings herein, an inlet flow route extends while a diameter thereof gradually decreases toward a position shifted from the center of an internal flow route. Accordingly, a vortex can be generated while flow velocity of a liquid of the internal flow route can be increased. Therefore, the liquid of the internal flow route can be smoothly collected, and the liquid can be smoothly injected into the internal flow route. Congestion of the liquid in the internal flow route can be reliably prevented.

According to the teachings herein, the rubber member includes a slit through which the inside and the outside of the internal flow route communicate with each other. Accordingly, a distal end of a puncture tube or a syringe can be smoothly inserted. Therefore, the blood can be safely collected, and a drug can be safely injected.

According to the teachings herein, the outlet flow route extends while a diameter thereof gradually decreases toward the position shifted from the center of the internal flow route. Accordingly, it is possible to reliably prevent the congestion of the liquid in the internal flow route. Even in a case where the inlet flow route and the outlet flow route are reversely connected to each other, the congestion can be prevented while a vortex can be reliably generated in the internal flow route.

According to the teachings herein, the inlet flow route and the outlet flow route have a symmetrical shape with respect to the center of the internal flow route, while respective connection portions connected to a circulation line are coaxially formed. Accordingly, without a need to increase dimensions of a main body, the vortex can be reliably generated in the internal flow route, and the congestion of the liquid in the internal flow route can be reliably prevented.

According to the teachings herein, the circulation line includes a blood circuit, which extracorporeally circulates and purifies blood of a patient. Accordingly, the blood of the internal flow route can be smoothly collected, and the liquid can be smoothly injected into the internal flow route. The congestion of the blood in the internal flow route can be reliably prevented.

BRIEF DESCRIPTION OF DRAWINGS

FIGS. 12(a) and 12(b) are schematic views illustrating a co-injection member according to another embodiment of the present invention.

FIGS. 13(a) and 13(b) are schematic views stating a co-injection member according to another embodiment of the present invention.

FIGS. 14(a) and 14(b) are schematic views illustrating a co-injection member according to another embodiment of the present invention.

DETAILED DESCRIPTION

Hereinafter, an embodiment according to the present invention will be described in detail with reference to the drawings.

A co-injection member according to the present embodiment is connected to a flexible tube configuring a blood circuit (circulation line of a liquid) for extracorporeally circulating and purifying blood of a patient. As illustrated in FIGS. 1 to 7, the co-injection member is configured to have a main body 2 having a connection portion 2a and a connection portion 2b formed therein, an internal flow route α, an inlet flow route A, an outlet flow route B, a cap 3, and a rubber member 4. The reference numeral P in the drawing represents the center of the internal flow route α, the reference numeral C1 represents a central line in a longitudinal direction (liquid flowing direction) of the main body 2, the reference numeral C2 represents a height direction of the main body 2, and the reference numeral C3 represents a width direction of the main body 2.

The main body 2 includes a resin product, for example, which can be connected to a blood circuit through which blood circulates (circulation line through which a liquid circulates), and is configured to have the connection portions 2a and 2b into which the flexible tube configuring the blood circuit is inserted for connection, the internal flow route α which is formed in a substantially central portion, the inlet flow route A through which the internal flow route α and the connection portion 2a communicate with each other, and the outlet flow route B through which the internal flow route α and the connection portion 2b communicate with each other.

The internal flow route α is formed at a substantially central position inside the main body 2, and the blood (liquid) of the blood circuit can circulate therethrough. The internal flow route α is formed so as to communicate with each of the inlet flow route A and the outlet flow route B. The inlet flow route A and the outlet flow route B include a flow route formed inside the main body 2, and are configured so that in a state where the blood circuit is connected to the connection portions 2a and 2b, the inlet flow route A can introduce the blood of the blood circuit (upstream side of a portion to which the co-injection member 1 is connected) into the internal flow route α, and the outlet flow route B can discharge the blood of the internal flow route α to the blood circuit (downstream side of the portion to which the co-injection member 1 is connected).

In addition, an opening 2c (refer to FIG. 4), which is open in a circular shape, is formed in a portion having the internal flow route α formed in the main body 2. A configuration is adopted in which the internal flow route α can face outward via the opening 2c in a state where the rubber member 4 is detached therefrom. A configuration is adopted in which the cap 3 is fixedly fitted to the opening 2c. The rubber member 4 is attached between the opening 2c and the cap 3, and a surface of the rubber member 4 is caused to face outward by an opening 3a formed in the cap 3.

Figure 8:
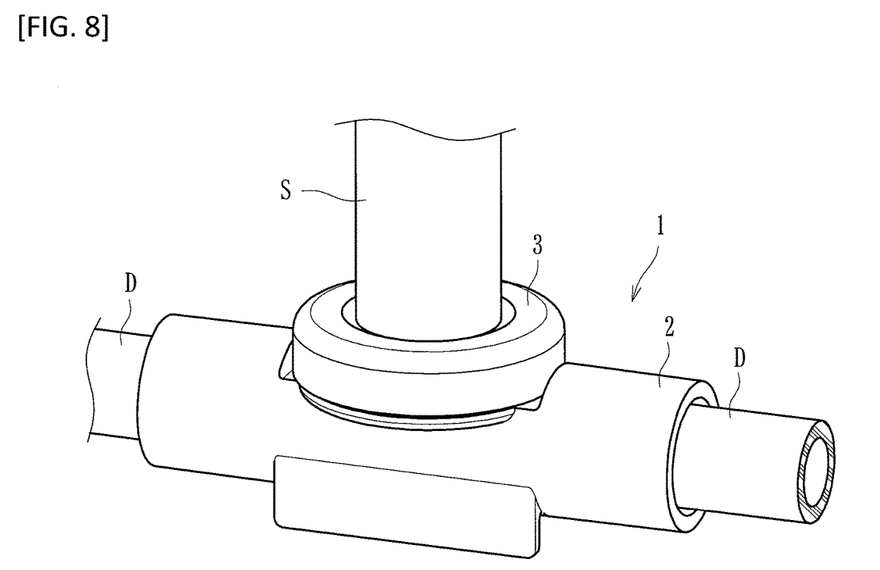
FIG. 8 is a perspective view illustrating a state where a distal end of a syringe is inserted into the co-injection member.
Figure 9:
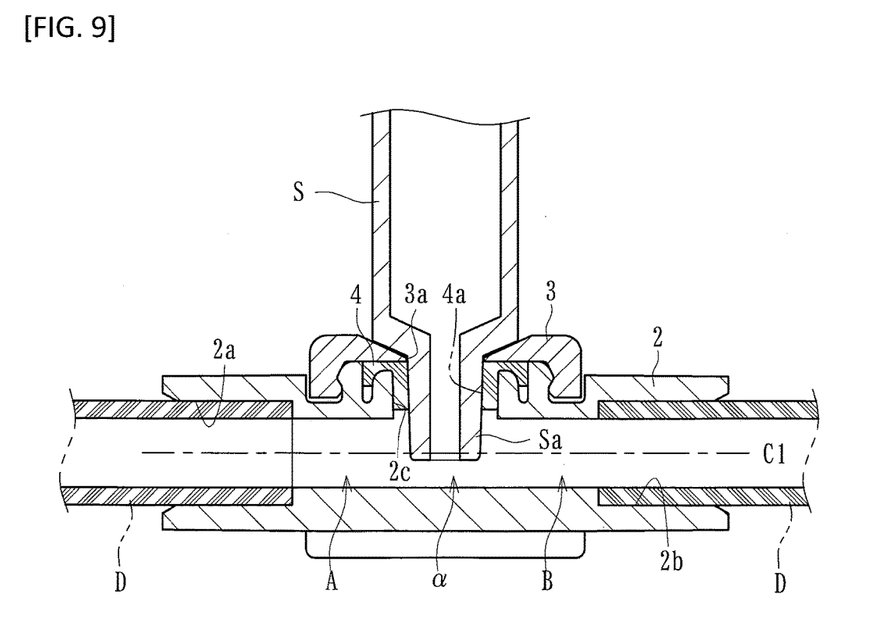
FIG. 9 is a sectional view illustrating the state where the distal end ne syringe is inserted into the co-injection member.

The rubber member 4 separates the inside and the outside of the internal flow route α, while having elasticity and maintaining the internal flow route in a liquid-tight manner. A slit 4a through which the inside and the outside of the internal flow route α communicate with each other is formed in substantially the center of the rubber member 4. Then, a distal end Sa of a syringe S (also similarly applied to other connection means such as a puncture tube) is pressed against the slit 4a so as to spread out the slit 4a. In this manner, as illustrated in FIGS. 8 and 9, the distal end Sa of the syringe S can be inserted into the internal flow route α via the slit 4a, thereby adopting a configuration in which the blood flowing in the internal flow route α can be collected or the drug can be injected into the internal flow route α. The present embodiment employs the rubber member 4 having the slit 4a formed therein. However, without disposing the slit 4a, the blood may be collected or the drug may be injected by an injection needle puncturing the rubber member 4.

Figure 1:
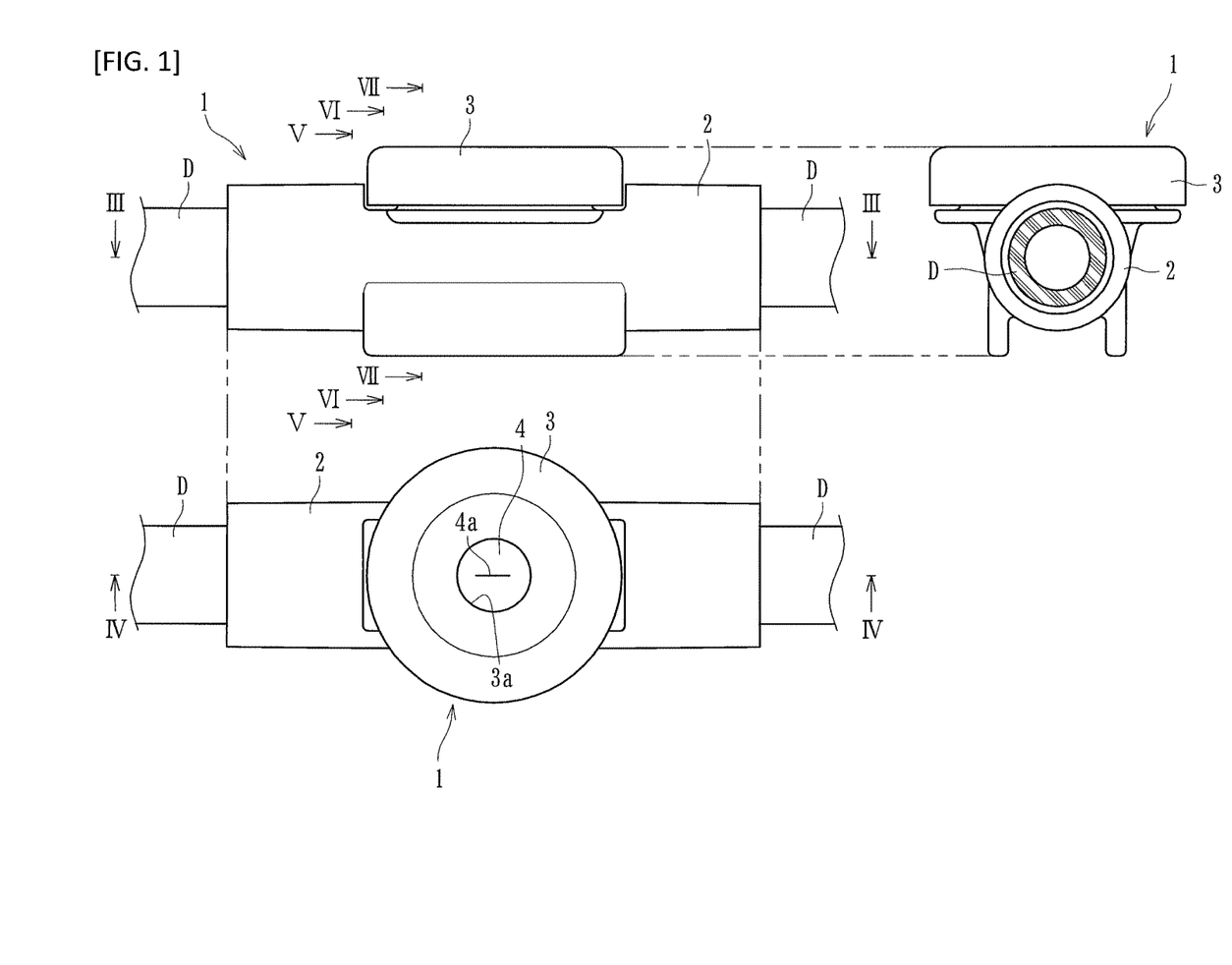
FIG. 1 illustrates a front view, a plan view, and a side view of a co-injection member according to an embodiment of the present invention.
Figure 2:
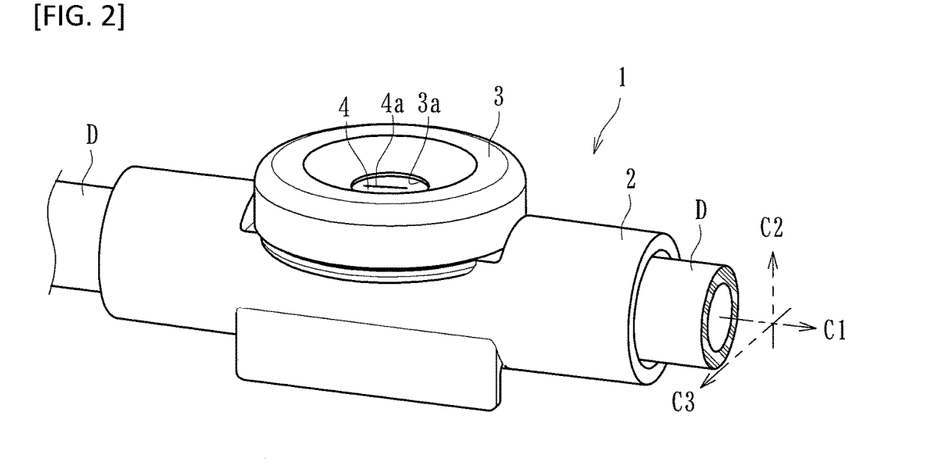
FIG. 2 is a perspective view illustrating the co-injection member
Figure 3:
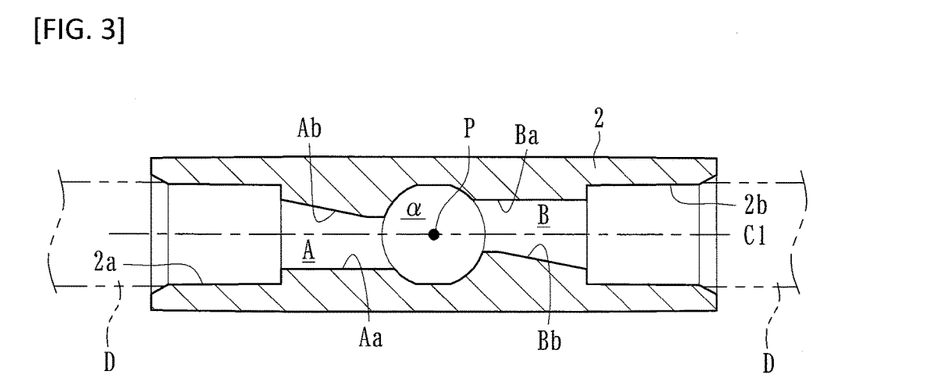
FIG. 3 is a sectional view taken along line in III-III FIG. 1.
Figure 4:
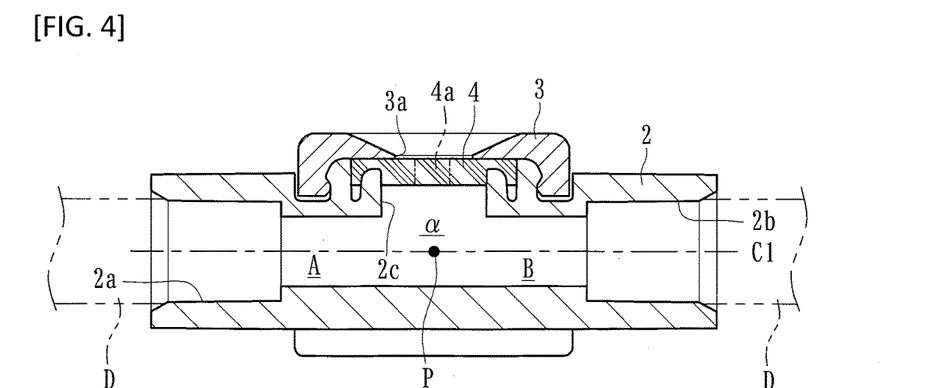
FIG. 4 is a sectional view taken along line IV-IV in FIG. 1.

Here, the inlet flow route A and the outlet flow route B according to the present embodiment are respectively formed toward the internal flow route α from the connection portions 2a and 2b. As illustrated in FIG. 3, the inlet flow route A and the outlet flow route B extend while a diameter thereof gradually decreases toward a position shifted from a center P of the internal flow route α. Specifically, it is preferable that each diameter decreasing rate (in a case where the diameter does not decrease, the rate is set to 0%) of the inlet flow route A and the outlet flow route B is 5% to 70%. Furthermore, it is most preferable that the diameter decreasing rate is 20% to 50%. According to the present embodiment, the inlet flow route A and the outlet flow route B extend while the diameter gradually decreases toward the position shifted from the center P of the internal, flow route α in a plan view (in the width direction (direction C3 in FIG. 2) of the main body 2). However, the diameter may gradually decrease in a front view (in the height direction (direction C2 in FIG. 2) of the main body 2).

Figure 5:
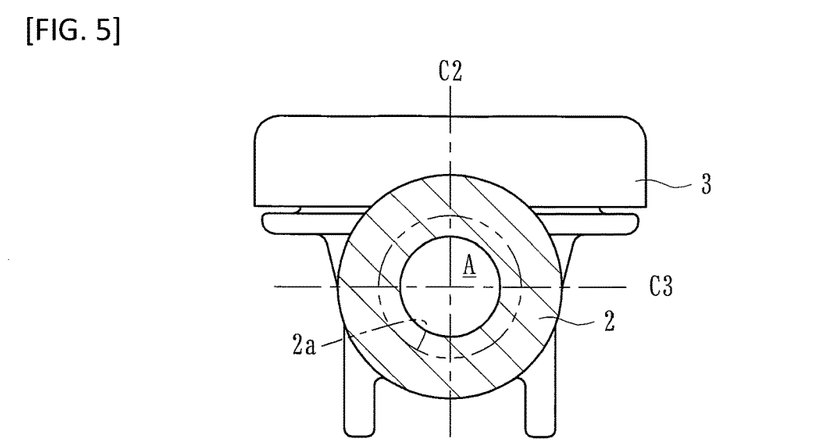
FIG. 5 is a sectional view taken along line V-V in FIG. 1.
Figure 6:
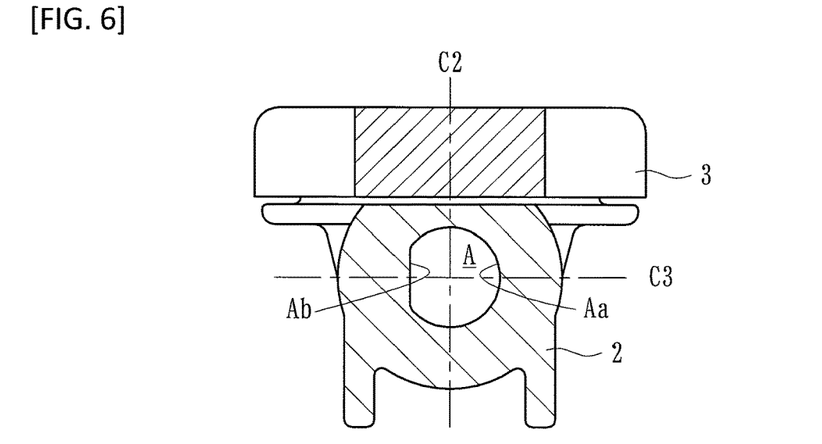
FIG. 6 is a sectional view taken along line VI-VI in FIG. 1.
Figure 7:
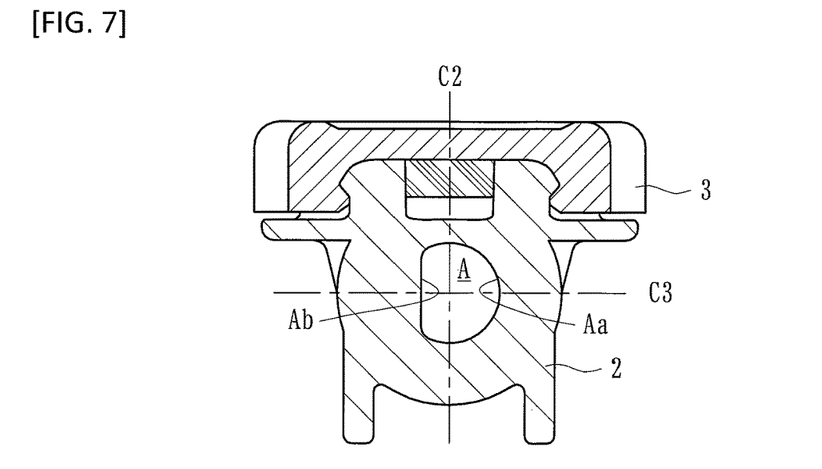
FIG. 7 is a sectional view taken along line VII-VII in FIG. 1.

More specifically, as illustrated in FIGS. 5 to 7, the inlet flow route A (also similarly applied to the outlet flow route B) has a gradient surface Ab (gradient surface Bb in the outlet flow route B) formed on one side on a flow route wall surface Aa (wall surface Ba in the outlet flow route B). The inlet flow route A is configured so that the diameter gradually decreases on the way to extend from the connection portion 2a (connection portion 2b in the outlet flow route B) toward the internal flow route α. According to the present embodiment, the gradient surface Ab (gradient surface Bb) is parallel to the direction C2. However, the diameter may be decreased by forming the gradient surface on a surface which is parallel to the direction C3.

Figure 10A:
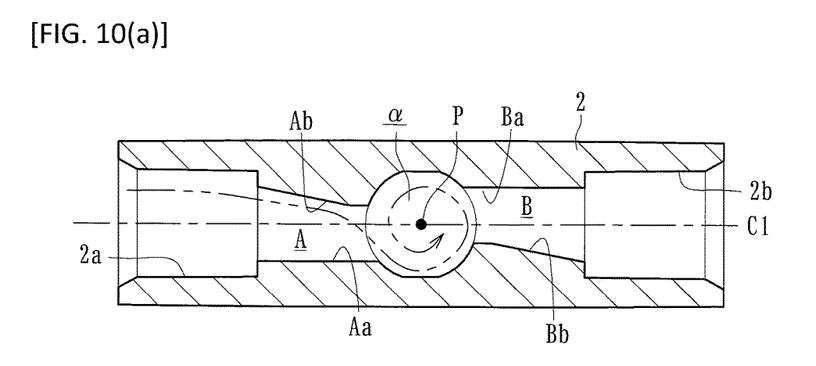
FIGS. 10(a) and 10(b) are schematic views illustrating a vortex formed in an internal flow route of the co-injection member.
Figure 10B:
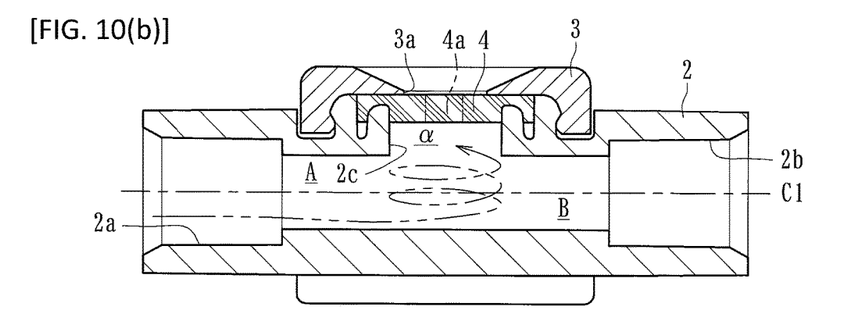

As illustrated in FIGS. 10(a) and 10(b), the blood flowing in the inlet flow route A is introduced into the internal flow route α while flow velocity thereof increases, and a vortex is generated in the internal flow route α. The vortex whose flow velocity increases is generated over the entire area of the internal flow route α. In particular, the vortex can be caused to reliably reach a portion surrounded by the opening 2c where the liquid is likely to become congested. Then, the blood generating the vortex inside the internal flow route α is discharged by bye the outlet flow route B, thereby decreasing the velocity in a process where the blood flows in the outlet flow route B.

Furthermore, according to the present embodiment, as rated in FIG. 3, the inlet flow route A and the outlet flow route B have a shape symmetrical (point symmetry) with respect to the center P of the internal flow route α while the connection portions 2a and 2b of the blood circuit (circulation line) are coaxially formed (coaxial on C1 serving as the central axis). In this manner, without a need to increase dimensions of the main body 2, the vortex of the internal flow route α can be reliably generated. Therefore, it is possible to reliably prevent congestion of the blood (liquid) in the internal flow route α.

Figure 11:
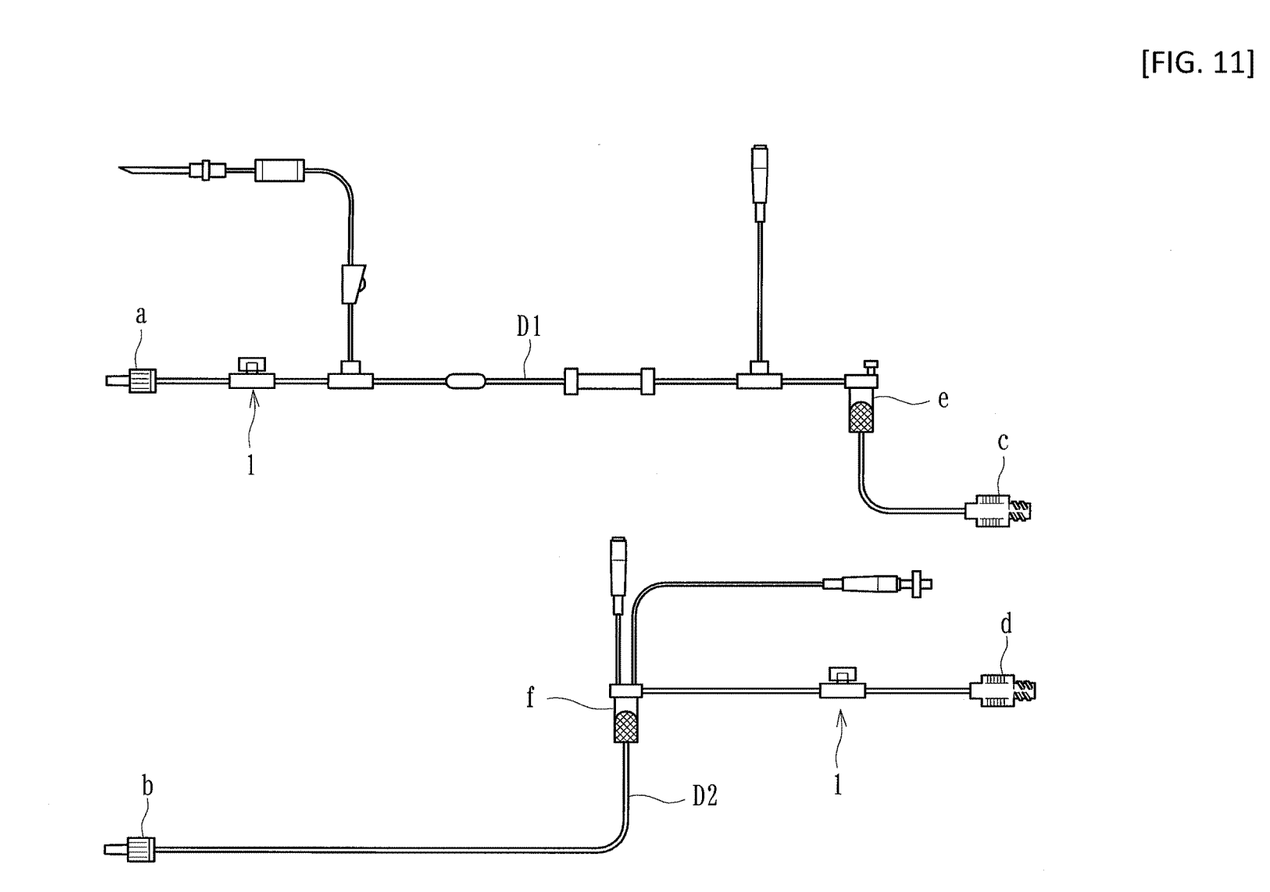
FIG. 11 is a schematic view illustrating blood circuit to which the co-injection member is connected.

On the other hand, as illustrated in FIG. 11, the co-injection member 1 is connected to the blood circuit, which has an arterial blood circuit D1 and a venous blood circuit D2, for extracorporeally circulating blood of a patient. That is, this co-injection member 1 is connected to each of the arterial blood circuit D1 and the venous blood circuit D2, For example, the co-injection member 1 can collect the blood (before blood purification), which extracorporeally circulates in the co-injection member 1, attached to an intermediate portion of the arterial blood circuit D1, and can inject a drug or a physiological saline solution into the blood (after blood purification) which extracorporeally circulates in the co-injection member 1 attached to an intermediate portion of the venous blood circuit D.

The arterial blood circuit D1 has a shunt connector a in which an arterial puncture needle can be attached to a distal end thereof. An arterial air trap chamber e is connected to an intermediate portion thereof. A proximal end thereof has a dialyzer connection portion c which can be connected to an arterial connection, portion of a blood purification device (dialyzer). in addition, the venous blood circuit D2 has a shunt connector b in which a venous puncture needle can be attached to a distal end thereof. A venous air trap chamber f is connected to an intermediate portion thereof A proximal end thereof has a dialyzer connection portion d which can be connected to a venous connection portion of the blood purification device (dialyzer).

According to the above-described embodiment since the inlet flow route A extends while the diameter thereof gradually decreases toward the position shifted from the center P of the internal flow route α, the vortex can be generated while the flow velocity of the liquid of the internal flow route α can be increased. Therefore, the liquid (blood) of the internal flow route α can be smoothly collected, and the liquid (the drug or the physiological saline solution) can be smoothly injected into the internal flow route α, and the congestion of the liquid in the internal flow route α can be reliably prevented. The rubber member 4 according to the present embodiment includes the slit 4a through which the inside and the outside of the internal flow route α communicate communicate with each other. Accordingly, the distal end of the puncture tube or the syringe can be smoothly inserted. Therefore, the blood can be safely collected, and the drug can be safely injected.

In addition, according to the present embodiment, similarly to the inlet flow route A, the outlet flow route B extends while the diameter thereof gradually decreases toward the position shifted from the center P of the internal flow route α. Accordingly, the congestion of the liquid (blood) in the internal flow route α can be more reliably prevented. Even in a case where the inlet flow route A and the outlet flow route B are reversely connected (the connection portion 2b is connected to the upstream side of the circulation line while the connection portion 2a is connected to the downstream side of the circulation tine) it is possible to prevent the congestion by reliably generating the vortex in the internal flow route α, Furthermore, the circulation line according to the present embodiment includes the blood circuit (the arterial blood circuit Dl and the venous blood circuit D2) for extracorporeally circulating and purifying the blood of the patient. Accordingly, the blood of the internal flow route α can be smoothly collected, and the liquid can be smoothly injected into the internal flow route α. The congestion of the blood in the internal flow route α can be reliably prevented. The position for attaching the co-injection member 1 and the number of attached co-injection members 1 are not limited to those according to the present embodiment. Any desired portion and any desired number may be employed for connection.

Hitherto, the present embodiment has been described. However, without being limited thereto, any configuration may be sufficiently adopted as long as at least the inlet flow route A has the diameter which gradually decreases toward the position shifted from the center P of the internal flow route α. The outlet flow route B may have the diameter which gradually decreases toward the center of the internal flow route α. Alternatively, the outlet flow route B may extend toward the position shifted from the center P of the internal flow route α while maintaining the dimensions of the same diameter, In addition, according to the present embodiment, the diameter is decreased by forming the gradient surfaces (Ab and Bb) in a portion on the flow route wall surfaces (Aa and Ba). However, the diameter may be decreased simply by gradually decreasing the diameter without forming the gradient surface.

Figure 12A:
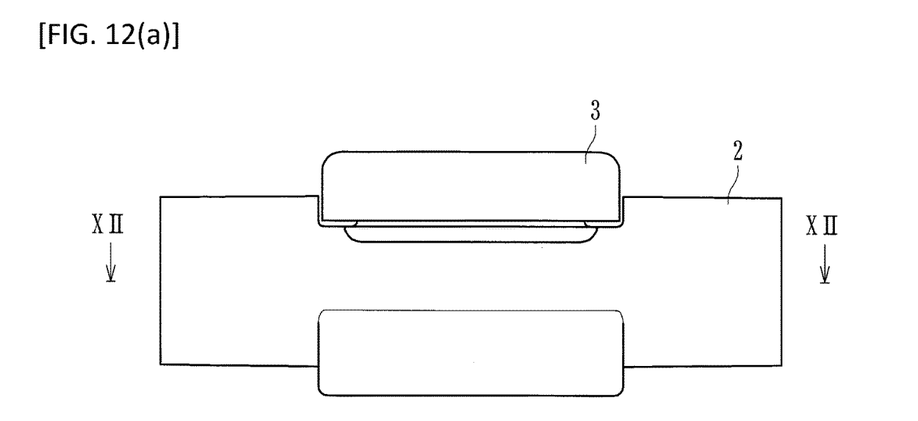
FIG. 12(a) is a front view.
Figure 12B:
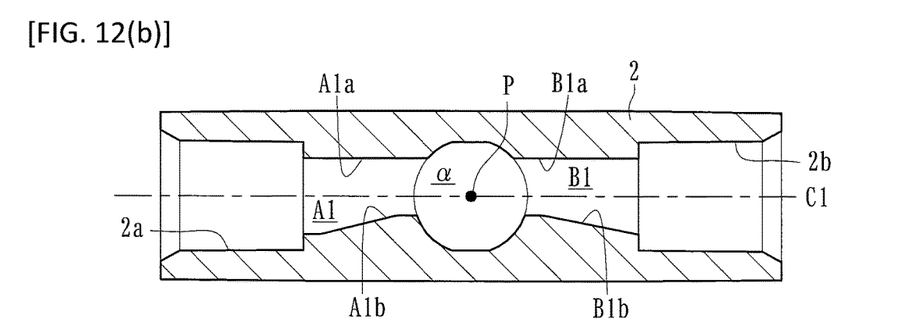
FIG. 12(b) is a sectional view taken along line XII-XII.
Figure 13A:
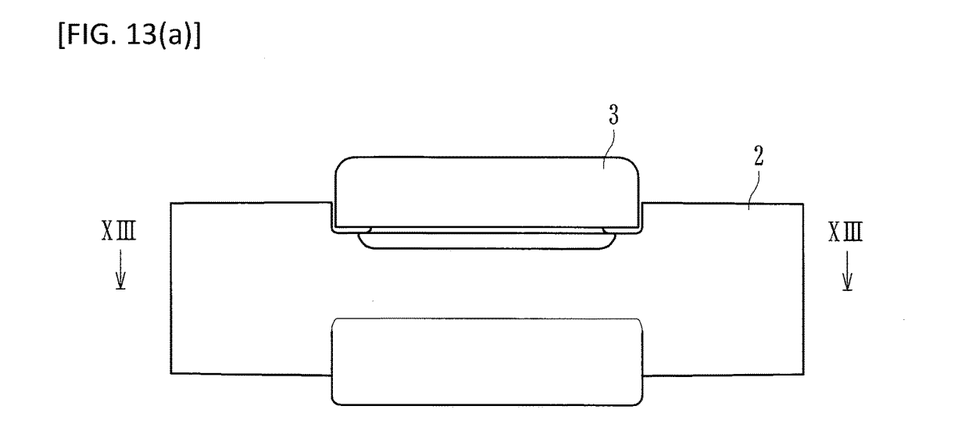
FIG. 13(a) is a front view.
Figure 13B:
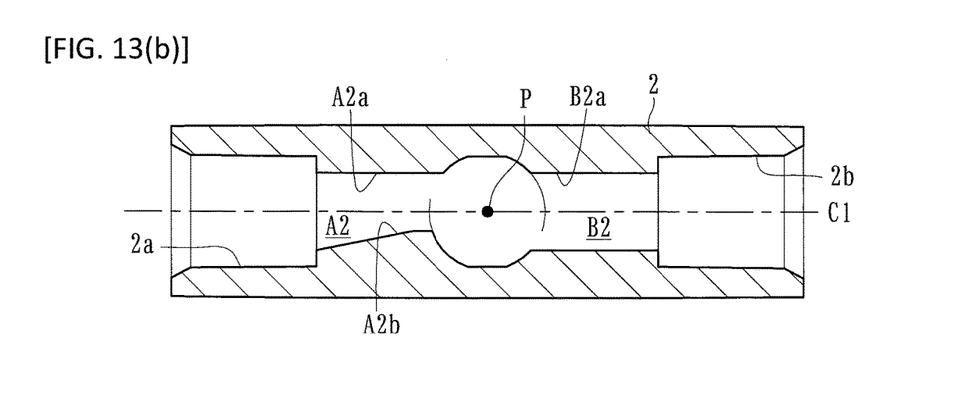
FIG. 13(b) is a sectional view taken along line XIII-XIII.

Furthermore, for example, as illustrated in FIGS. 12(a) and 12(b), another embodiment may be adopted in which a gradient surface A1b formed on a flow route wall surface A1a in an inlet flow route A1, and a gradient surface B1b formed on a flow route wall surface B1a in an outlet flow route B1, may be formed on the same side with respect to the central axis (C1). in addition, as illustrated in FIGS. 13(a) and 13(b), a gradient surface A1b may be formed on a flow route wall surface A2a in an inlet flow route A2. In contrast, a gradient surface may not be formed on a flow route wall surface B2a in an outlet flow route B2 (that is, the inlet flow route A2 may extend while the diameter thereof decreases in a direction shifted from the center P, and the outlet flow route B2 may extend toward the center P while maintaining the same diameter).

Figure 14A:
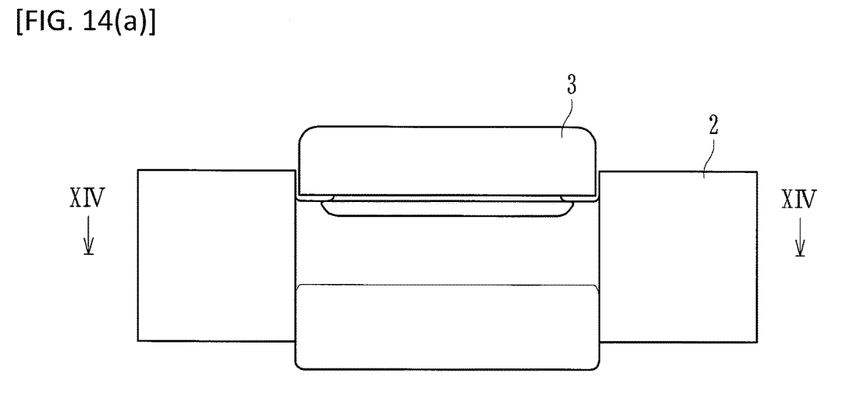
FIG. 14(a) is a front view.
Figure 14B:
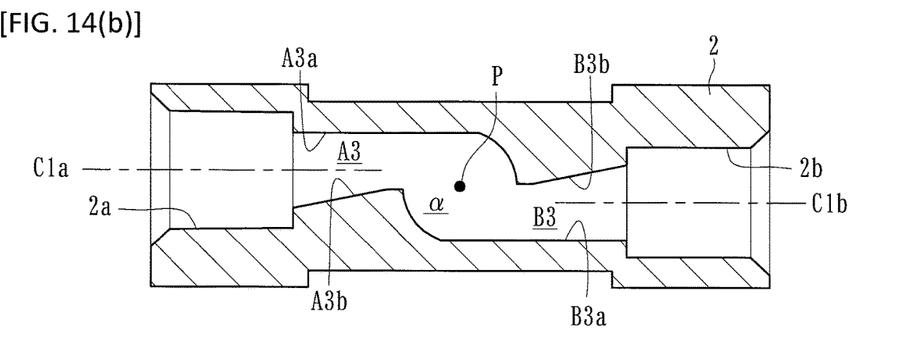
FIG. 14(b) is a sectional view taken along line XIV-XIV.

Furthermore, as illustrated in FIGS. 14(a) and 14(b), a gradient surface A3b may be formed on a flow route wall surface A3a in an inlet flow route A3, and a gradient surface B3b may be formed on a flow route wall surface 83a in an outlet flow route B3. The inlet flow route A3 and the outlet flow route 83 may extend from connection portions of central axes C1a and C1b which are different from each other (connection portions connected to the circulation line may not be coaxially formed). In this case, since dimensions increase in the width direction of the main body 2, a vortex in the internal flow route α can be more reliably formed.

Without being limited to the present embodiment, a shape or an attachment component of the co-injection member 1 may be applied to various forms (for example, those which have different shapes of the slit or the cap). Furthermore, the co-injection member 1 applied to the present embodiment is connected to the blood circuit for extracorporeally circulating and purifying the blood of the patient. However, the co-injection member can be connected to a flow route (transfusion line etc.) of other liquids.

As long as an inlet flow route extends while a diameter thereof gradually decreases toward a position shifted from the center of an internal flow route, a co-injection member can also be applied to those which have different external shapes or those which have other added functions.

REFERENCE SIGNS LIST

1 CO-INJECTION MEMBER
2 MAIN BODY
3 CAP
4 RUBBER MEMBER
α INTERNAL FLOW ROUTE
A INLET FLOW ROUTE
B OUTLET FLOW ROUTE

The invention claimed is:
1. A co-injection member comprising:
a main body that can be connected to a circulation line through which a liquid is circulated;
an internal flow route that is formed inside the main body, and that can circulate the liquid of the circulation line;
an inlet flow route that is formed inside the main body, and that can introduce the liquid into the internal flow route;
an outlet flow route that is formed inside the main body, and that can discharge the liquid of the internal flow route; and
a rubber member that is attached to an opening formed in the main body, and that separates an inside and an outside of the internal flow route from each other,
wherein the co-injection member can collect the liquid of the internal flow route and can inject another liquid into the internal flow route via the rubber member;
wherein the inlet flow route extends towards a position shifted from a center axis extending through the inlet flow route and the outlet flow route and also shifted in a direction perpendicular to a center axis of the opening of the main body, while an inner channel of the inlet flow route gradually decreases in a width direction of the main body substantially perpendicular to the center axis of the opening of the main body; and
wherein the co-injection member is configured so that a vortex is generated to direct the internal flow route and flow velocity of the liquid of the internal flow route is increased.

2. The co-injection member according to claim 1, wherein the rubber member includes a slit through which the inside and the outside of the internal flow route communicate with each other.

3. The co-injection member according to claim 2, wherein the outlet flow route extends while a diameter thereof gradually decreases toward the position shifted from the center of the internal flow route.

4. The co-injection member according to claim 3, wherein the circulation line includes a blood circuit which extracorporeally circulates and purifies blood of a patient.

5. The co-injection member according to claim 2, wherein the circulation line includes a blood circuit which extracorporeally circulates and purifies blood of a patient.

6. The co-injection member according to claim 1, wherein the outlet flow route extends while a diameter thereof gradually decreases toward the position shifted from the center of the internal flow route.

7. The co-injection member according to claim 6, wherein the inlet flow route and the outlet flow route have a symmetrical shape with respect to the center of the internal flow route, while respective connection portions connected to the circulation line are coaxially formed.

8. The co-injection member according to claim 7, wherein the circulation line includes a blood circuit which extracorporeally circulates and purifies blood of a patient.

9. The co-injection member according to claim 6, wherein the circulation line includes a blood circuit which extracorporeally circulates and purifies blood of a patient.

10. The co-injection member according to claim 6, wherein a diameter decreasing rate is 20% to 50%.

11. The co-injection member according to claim 6, wherein the diameter is decreased by forming a gradient surface in a portion on a flow route wall surface of the inlet flow route and forming a gradient surface in a portion on a flow route wall surface of the outlet flow route.

12. The co-injection member according to claim 6, wherein the diameter is decreased by gradually decreasing the diameter without forming a gradient surface.

13. The co-injection member according to claim 6, wherein the inlet flow route and the outlet flow route do not have a symmetrical shape with respect to the center of the internal flow route and respective connection portions connected to the circulation line are not coaxially formed.

14. The co-injection member according to claim 1, wherein the circulation line includes a blood circuit which extracorporeally circulates and purifies blood of a patient.

15. The co-injection member according to claim 1, wherein a diameter decreasing rate is 20% to 50%.

16. The co-injection member according to claim 1, wherein the outlet flow route extends toward the position shifted from the center of the internal flow route while maintaining dimensions of a same diameter.

17. The co-injection member according to claim 1, wherein an axis of the vortex and an axis of the opening of the main body are coaxial.

\* \* \* \* \*